United States Patent
Otano et al.

(10) Patent No.: US 11,620,552 B2
(45) Date of Patent: Apr. 4, 2023

(54) MACHINE LEARNING MODEL FOR PREDICTING AN ACTION TO BE TAKEN BY AN AUTISTIC INDIVIDUAL

(71) Applicant: International Business Machines Corporation, Armonk, NY (US)

(72) Inventors: Tomas Carlos Otano, Jalisco (MX);
Daniel Herrera Salgado, Jalisco (MX);
Ricardo Noyola Picazzo, Jalisco (MX);
Karen Barba Munguia, Jalisco (MX);
Jorge Luis Gonzalez Sanchez, Jalisco (MX)

(73) Assignee: International Business Machines Corporation, Armonk, NY (US)

( * ) Notice: Subject to any disclaimer, the term of this patent is extended or adjusted under 35 U.S.C. 154(b) by 1141 days.

(21) Appl. No.: 16/163,652

(22) Filed: Oct. 18, 2018

(65) Prior Publication Data

US 2020/0125976 A1 Apr. 23, 2020

(51) Int. Cl.
*G06N 5/04* (2023.01)
*G06N 3/08* (2023.01)
(Continued)

(52) U.S. Cl.
CPC .............. *G06N 5/046* (2013.01); *G06F 3/017* (2013.01); *G06N 3/0454* (2013.01); *G06N 3/08* (2013.01);
(Continued)

(58) Field of Classification Search
CPC ........ G06N 5/046; G06N 3/0454; G06N 3/08; G06N 3/0445; G06N 3/0481; G06F 3/017;
(Continued)

(56) References Cited

U.S. PATENT DOCUMENTS 6,816,836 B2 11/2004 Basu et al.
7,171,043 B2 1/2007 Nefian
(Continued)

FOREIGN PATENT DOCUMENTS

CN 103794110 A 5/2014

OTHER PUBLICATIONS

Gentry et al, "Personal digital assistants as cognitive aids for high school students with autism: Results of a community-based trial," Journal of Vocational Rehabilitation 32 (2010) 101-107, DOI: 10.3233/JVR-2010-0499, 8 pages.
(Continued)

*Primary Examiner* — Beau D Spratt
*Assistant Examiner* — Parmanand D Patel
(74) *Attorney, Agent, or Firm* — Patterson + Sheridan, LLP (57) ABSTRACT

Method and apparatus for predicting an action to be taken by a user of a mobile device, comprising: generating a machine learning (ML) model using historical training data comprising (a) output training data that includes a scheduled action on a calendar and (b) input training data comprising historical usage data of the mobile device by the user; receiving real-time usage data of the mobile device, the real-time usage data indicating at least one of (a) an emotional state of the user, wherein the emotional state is indicative of autism spectrum disorder, or (b) indicators of the environment of the user; and evaluating data comprising the real-time usage data of the mobile device using the ML model to output a suggested action to be performed by the user, wherein the suggested action mitigates a negative impact on the user of a symptom of the autism spectrum disorder.

20 Claims, 4 Drawing Sheets

(51) Int. Cl.
 *G06N 3/04* (2023.01)
 *G06F 3/01* (2006.01)
 *G10L 15/26* (2006.01)
 *G06N 5/046* (2023.01)
(52) U.S. Cl.
 CPC ........ *G10L 15/26* (2013.01); *G06F 2203/011* (2013.01)
(58) Field of Classification Search
 CPC .. G06F 2203/011; G06F 3/0346; G10L 15/26; G09B 19/00; G16H 20/70; G16H 50/20
 See application file for complete search history.

(56) References Cited

U.S. PATENT DOCUMENTS

| | | | |
|---|---|---|---|
| 7,217,133 B2 | 5/2007 | Thomas et al. | |
| 7,629,123 B2 | 12/2009 | Millonig et al. | |
| 8,356,035 B1 | 1/2013 | Baluja et al. | |
| 8,708,702 B2 | 4/2014 | Paul | |
| 9,747,900 B2 | 8/2017 | Zurek et al. | |
| 2003/0187652 A1 | 10/2003 | Fairman | |
| 2004/0193415 A1 | 9/2004 | Chaudhari et al. | |
| 2005/0112534 A1 | 5/2005 | McCarton et al. | |
| 2005/0131744 A1 | 6/2005 | Brown et al. | |
| 2007/0071209 A1* | 3/2007 | Horvitz | G06Q 10/109 379/201.06 |
| 2007/0083366 A1* | 4/2007 | Peters | G10L 15/26 704/235 |
| 2011/0229862 A1 | 9/2011 | Parikh | |
| 2013/0216989 A1* | 8/2013 | Cuthbert | A61B 5/1113 434/238 |
| 2014/0379352 A1* | 12/2014 | Gondi | G10L 25/63 704/271 |
| 2016/0351074 A1 | 12/2016 | Paul et al. | |
| 2017/0372267 A1* | 12/2017 | Soffer | G06Q 10/1095 |
| 2019/0050774 A1* | 2/2019 | Divine | G16H 50/20 |
| 2019/0282155 A1* | 9/2019 | St Amant | G16H 40/63 |
| 2021/0361227 A1* | 11/2021 | Chou | G06N 20/00 |

OTHER PUBLICATIONS

Spain et al., "Cognitive behaviour therapy for social anxiety in autism spectrum disorder: a systematic review," Emerald Insight, Dated: Jan. 3, 2017, pp. 1-2.

Rogers et al., "Helping Young Children with Autism Spectrum Disorder Develop Social Ability: The Early Start Denver Model Approach," Handbook of Social Skills and Austism Spectrum Disorder, Date: Oct. 17, 2017, pp. 197-222 [Abstract Only].

Aresti-Bartolome N, Garcia-Zapirain B. Technologies as support tools for persons with autistic spectrum disorder: a systematic review. Int J Environ Res Public Health. 2014;11(8):7767-7802. Published Aug. 4, 2014.

* cited by examiner

MACHINE LEARNING MODEL FOR PREDICTING AN ACTION TO BE TAKEN BY AN AUTISTIC INDIVIDUAL

BACKGROUND

The present invention relates to machine learning models, and more specifically, to training a machine learning model on the routine of an individual, such as an autistic individual, so as to assist the individual with daily tasks.

Autistic individuals, especially children, often struggle with daily routines. For example, an autistic child may struggle realizing that it is time to make a phone call to a parent, or may struggle realizing that it is time to wait for a school bus or go to the bathroom. Given that many autistic children avoid human contact but are naturally attracted to devices, a need exists for solutions that utilize devices to assist autistic children in maintaining daily routines.

SUMMARY

According to one embodiment of the present invention, a method, system, and computer program product for predicting an action to be taken by a user of a mobile device, comprising receiving real-time usage data of the mobile device, the real-time usage data indicating at least one of (a) an emotional state of the user, wherein the emotional state is indicative of autism spectrum disorder, or (b) indicators of the environment of the user; and evaluating data comprising the real-time usage data of the mobile device using a machine learning (ML) model to output a suggested action to be performed by the user, wherein the suggested action mitigates a negative impact on the user of a symptom of the autism spectrum disorder, and further wherein the ML model is generated using historical training data comprising (a) output training data that includes a scheduled action on a calendar and (b) input training data comprising historical usage data of the mobile device by the user.

DETAILED DESCRIPTION

Embodiments herein describe techniques for scheduling events or actions for a person diagnosed with an autism spectrum disorder. Autism spectrum disorder ("ASD" or "autism") is a range of complex neurodevelopment disorders, characterized by social impairments, communication difficulties, and restricted, repetitive, and stereotyped patterns of behavior. A hallmark feature of autism is impaired social interaction. Techniques herein assist an autistic child in maintaining a daily routine by providing a machine learning model that learns about the child's behaviors that relate to the routine. The machine learning model then reminds the autistic child of actions or events that are to be performed, as per a healthy routine. Maintaining a healthy routine allows the autistic child to feel like he or she is in a secure environment, improving his or her quality of life.

Figure 1:
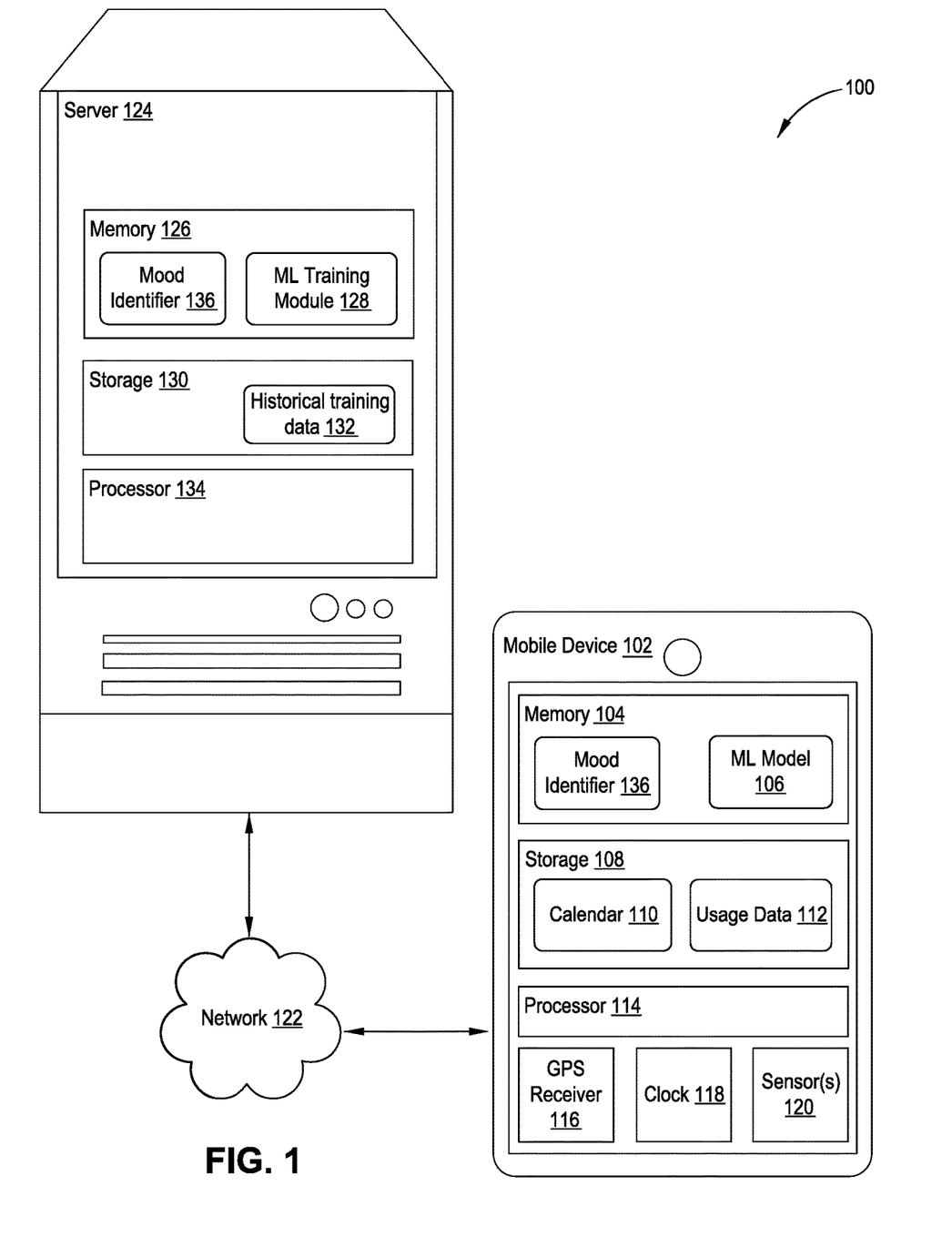
FIG. 1 depicts a block diagram of a computing system in which one or more embodiments of the present invention may be implemented.

FIG. 1 depicts a block diagram of a computing system 100 in which one or more embodiments of the present invention may be implemented. The computing system 100 comprises a server 124 and a mobile device 102 connected by a network 122. The network 122 may be a local area network or a wide area network, such as the Internet. The mobile device 102 may be, for example, a mobile phone, a personal digital assistant (PDA), or a smart watch. The server 124 may be, for example, a computer built using x86 architecture or other architecture (e.g., x64 architecture, quantum computer architecture). The server 124 can represent one computer device or multiple computing devices (e.g., a datacenter), may represent a virtual appliance such as a virtual machine, or may represent a cloud microservice.

The mobile device 102 comprises memory 104, storage 108, processor 114, a global positioning system (GPS) receiver 116, a clock 118, and one or more sensors 120. The memory 104 may include one or more random access memory modules that exist at multiple levels of a memory hierarchy and can range from high speed registers and caches to lower speed DRAM chips. The storage 108 may be a persistent storage device. Although the storage 108 is shown as a single unit, the storage 108 may be a combination of fixed and/or removable storage devices, such as fixed disc drives, solid state drives, or removable memory cards. The memory 104 and the storage 108 may be part of one virtual address space spanning multiple primary and secondary storage devices. The processor 114 is representative of a single central processing unit (CPU), multiple CPUs, a single CPU having multiple processing cores, and the like. The GPS receiver 116 is a device configured to receive information from GPS satellites and then to calculate geographical position of mobile device 102. The clock 118 is a device configured to measure and keep time. The sensor(s) 120 represent one or more sensors, such as for example, a microphone, a proximity sensor, ambient light sensor, camera, accelerometer, gyroscope, compass, barometer, and pressure sensitive display. Mobile device 102 may also include a network interface device (not shown) to connect to network 122 and communicate with devices on network 122.

Server 124 comprises memory 124, storage 130, and processor 134. The memory 124, the storage 130, and the processor 134 may be substantially as described above with respect to the memory 104, the storage 108, and the processor 114, respectively.

The memory 104 of mobile device 102 comprises a machine learning (ML) model 106 and mood identifier 136. The mood identifier 136 is a machine learning model trained on (a) historical input training data comprising location, time, and/or some or all sensor data, and (b) historical output training data of a mood of a user (not shown) of mobile device 102. As used herein, "mood data" or "data of a mood" is data that indicates the emotional state of the user of mobile device 102. The user may be an autistic individual, specifically an autistic child. The mood identifier 136 may then use real-time input data, which may be the same type of data as historical input training data, to predict or determine the mood of the user. In an embodiment, the historical input training data used to train the mood identifier 136 may include data from a voice-to-text engine (not shown), which converts sound data from a microphone of mobile device 102 to natural speech data. Natural speech data may include data that indicates mumbling or repetitive words. In conjunction, microphone data may indicate the volume of these words to indicate whether words were shouted, whispered, etc. The natural speech data may then be provided as a historical input data to the mood identifier 136 to train the mood identifier 136, or as real-time input data to predict or determine a current mood of the user.

For example, if the user of mobile device is repeating certain words while shouting, then this behavior might be associated with certain moods, such as hunger or anger. For another example, accelerometer and gyroscope data might indicate fidgeting or spasms, and might correspond to certain moods, such as frustration or excitement. For another example, the camera of the mobile device 102 may capture facial expressions of the user, and the facial expressions may be associated with certain emotions. The mood identifier may be trained to specifically identify moods that are common among autistic individuals, specifically, autistic children. Exemplary moods include sleepy, irritated, tense, confused, cheerful, relaxed, afraid, alarmed, excited, frustrated, thankful, cheerful, grouchy, anxious, etc.

Data used to train the mood identifier 136 may be obtained by, for example, collecting environment data such as location, time, and/or sensor data of the mobile device 102 for a time range, and then asking the user to identify his or her mood. The identified mood is then associated with the environment data through the training process of the mood identifier 136. The time range may be, for example, one second, five seconds, twenty seconds, a minute, five minutes, or ten minutes. For example, data may be collected for ten minutes and then the user may be asked to identify his or her mood, and the collected data is then associated with the mood. The collected data may be used as training input data, and the provided mood may be used as the training output data. The collection may be done repeatedly for a period of time, such as once a day for a number of days, or several times a day for a number of days. The collection may also be done at a specific time, such as for example, concurrently with the collection of data for ML model 106, as described below. For example, at the time or around the time of each scheduled action on the calendar 110, the mobile device 102 may ask the user to identify his or her mood.

In an embodiment, the historical input training data of mood identifier 136 may be the same usage data 112 and/or historical training data 132 as used to train ML model 106 described below, but instead of associating the historical input training data with a training output of a calendar action, the historical input training data is associated with a training output of a mood indicating an emotional state of the user.

Some or all data used to train the mood identifier 136 may also be obtained by manual creating the data. For example, as determined by psychologists, certain words spoken by the user may be associated with certain moods, and such associations may be created within mood identifier 136 by manually creating data that associates certain spoken words with certain moods. The collected and/or created data may then be used to train the mood identifier 136 to predict the mood of the user of the mobile device 102.

The mood identifier 136 may be a neural net. For example, the mood identifier 136 may be a feedforward neural network, a regulatory feedback neural network, a radial basis function neural network, a recurrent neural network, a modular neural network, or another type of neural network. As shown in FIG. 1, an instance of mood identifier 136 may be present on mobile device 102, and another instance of the mood identifier 136 may be present on the server 124.

The ML model 106 uses real-time environment data, such as location, time, and sensor data, and optionally also mood data of the user of mobile device 102, in order to predict or determine an action that is to be taken by the user of the mobile device 102. In an embodiment, ML model 106 may also use real-time mood data, such as that obtained from mood identifier 136, to predict or determine the action. In an embodiment, ML model 106 may use data from a voice-to-text engine, which converts sound data from a microphone of mobile device 102 to natural speech, and the natural speech may then be provided as an input to ML model 106 to predict or determine an action. The prediction or determination is generated after training ML model 106 by ML training module 128, as further described below with reference to FIG. 3. ML model 106 may be a neural net. For example, ML model 106 may be a feedforward neural network, a regulatory feedback neural network, a radial basis function neural network, a recurrent neural network, a modular neural network, or another type of neural network.

The storage 108 of mobile device 102 comprises a calendar 110 and usage data 112. The calendar 110 is a calendar of scheduled actions that are to be taken by user of mobile device 102. Exemplary scheduled actions may include: brush teeth, go to bathroom, go to bus stop and wait for school bus, do homework, go to kitchen to eat dinner, have snack, call father, check email, wash hands, take medication, etc. Each scheduled action within the calendar 110 is associated with a specific time at which that action is to be taken on that day, such as for example, 8:00 am, 12 pm, 3:30 pm, or 7:41 pm.

The usage data 112 comprises environment data, such as location data, time and/or a time range, data of some or all sensor(s) 120, and also comprises a scheduled action from calendar 110. The time range may be, for example, one second, five seconds, twenty seconds, a minute, five minutes, or ten minutes. The usage data 112 may be organized into a data structure, such as a table. Data in each row of the table may be associated or labeled with a scheduled action from the calendar 110.

In a first embodiment, collection of the usage data 112 begins at a predefined period of time before a scheduled action. The predefined period of time may be equal to the time range described above. For example, if an action is scheduled for 12:00 pm and the time period is ten minutes, then at 11:50 am, the mobile device 102 will begin recording data from sensor(s) 120, and also optionally from the GPS receiver 116 and the clock 118. Within the usage data 112, data corresponding to the scheduled action of this example may comprise the time of 12:00 pm, the time range of ten minutes, location data of mobile device 102 during the ten minute time range, location data of mobile device 102 at 12:00 pm, and data from some or all of sensor(s) 120 during the ten minute range. After collecting the usage data 112 associated with a scheduled action, mobile device 102 transmits the usage data 112 to server 124, where usage data 112 is added to historical training data 132. Usage data 112 may be transmitted to server 124 and/or combined with historical training data 132 after collection of data for each scheduled action, or after collection of data for several scheduled actions.

In a second embodiment, the usage data 112 comprises data obtained from continuous recordings of location, time, and sensor data, but the data is annotated such that the data recorded within a predefined time range before a scheduled action on the calendar 110 is annotated as data that is specifically associated with that scheduled action. In this second embodiment, the usage data 112 may be transmitted to the server 124 and/or combined with the historical training data 132 periodically, such as for example, every minute, every hour, every day, or every week.

The memory 126 of the server 124 comprises ML training module 128 and mood identifier 136. The ML training module 128 trains a neural network using historical training data 132 to generate the ML model 106, as described with respect to FIG. 3, below. The mood identifier 136 located on the server 124 operates substantially the same as the mood identifier 136 located on the mobile device 102, as described above.

The storage 130 of the server 124 comprises historical training data 132. The historical training data 132 comprises usage data 112 collected for a number of scheduled actions on the calendar 110. The number may be, for example, ten, one-hundred, one-thousand, or ten-thousand scheduled actions. When the server 124 receives the usage data 112 from the mobile device 102, the ML training module 128 combines the currently received usage data 112 with previously received usage date 112. The combined usage data 112 becomes the historical training data 132, which is used by the ML training module 128 to train and generate the ML model 106.

The historical training data 132 may comprise data obtained from processing usage data 112. For example, ML training module 128 may use a voice-to-text engine to convert sound data from a microphone of mobile device 102 to natural speech, which may then be used as data that is fed into a neural network to generate the ML model 106. For another example, ML training module 128 may use mood data from the mood identifier 136, and mood data may then be used to train a neural network and to generate the ML model 106.

In another embodiment, all software and data components of the server 124, such as the ML training module 128 and the historical training data 132 may be located within the mobile device 102 rather than in the server 124. In this embodiment, functions described herein as performed by the server 124 may instead be performed by the mobile device 102.

Figure 2:
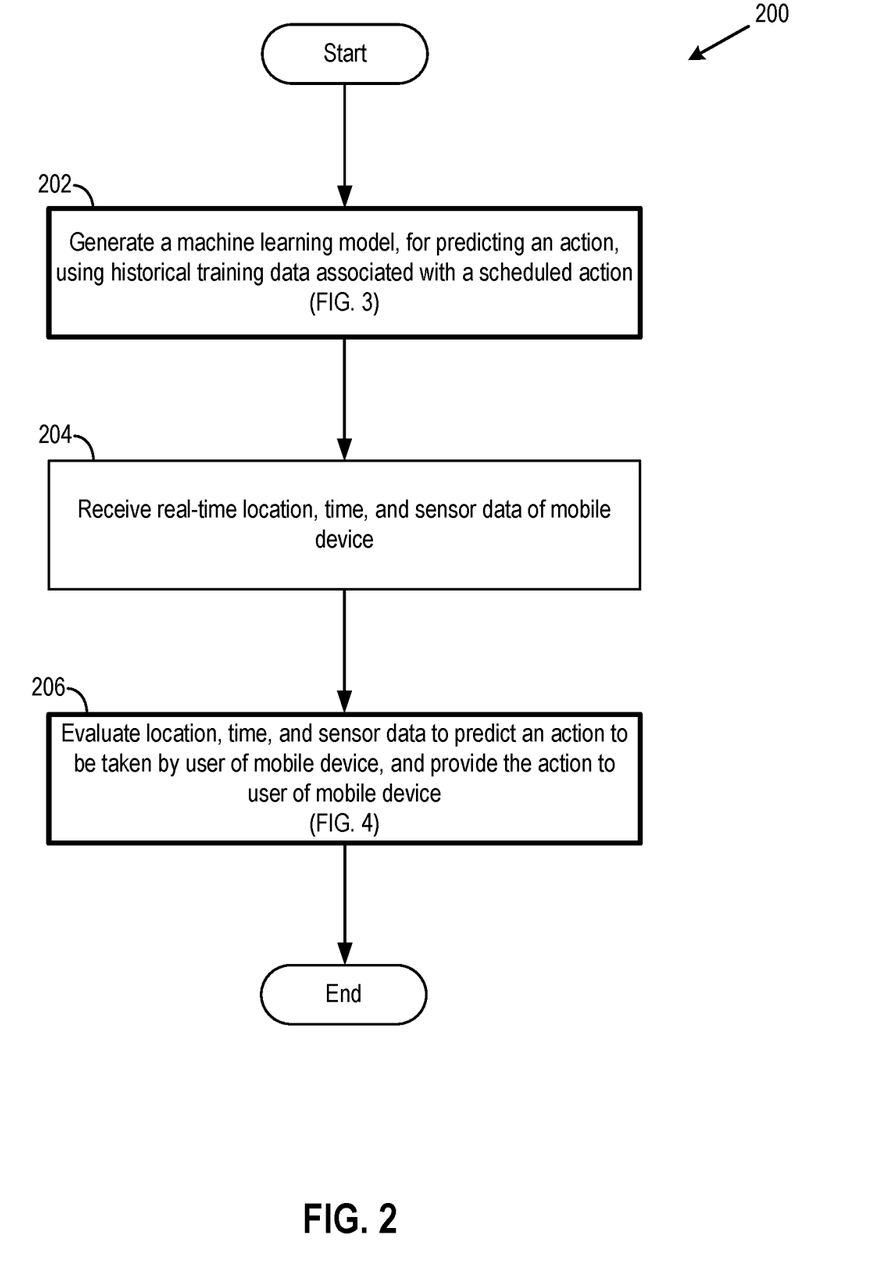
FIG. 2 depicts a flow diagram of a method of generating and training an ML model, providing the ML model with real-time data, and using the real-time data by the ML model to predict an action to be taken by a user of a mobile device, according to an embodiment.

FIG. 2 depicts a flow diagram of a method 200 of generating and training the ML model 106, providing the trained ML model 106 with real-time data, and using the real-time data by the trained ML model 106 to predict an action to be taken by a user of the mobile device 102, according to an embodiment. Method 200 is performed by a combination the components shown in FIG. 1.

At block 202, the ML model 106 is generated and trained using the historical training data 132. Block 202 is described in more detail below with reference to FIG. 3.

At block 204, the generated and trained ML model 106 receives real-time location, time, and sensor data of the mobile device 102. The real-time location, time, and sensor data may have been collected over a predefined period of time. The predefined period of time may be the same as the period of time during which data for the usage data 112 is collected before a scheduled action. The predefined period of time over which real-time data is collected may be, for example, one second, five seconds, twenty seconds, a minute, five minutes, or ten minutes.

At block 206, the real-time data received at block 204 is used as input into the generated and trained ML model 106, which evaluates the real-time data to predict or determine an action to be taken by a user of the mobile device 102, and to provide that action to the user. In an embodiment, the ML model 106 predicts an action to be taken by the user, and along with the prediction, provides a confidence score or likelihood of the prediction. In this embodiment, the action may be provided to the user only if the confidence score is above a predefined threshold confidence score, as further described with reference to FIG. 4, below. After block 206, the method 200 ends.

Figure 3:
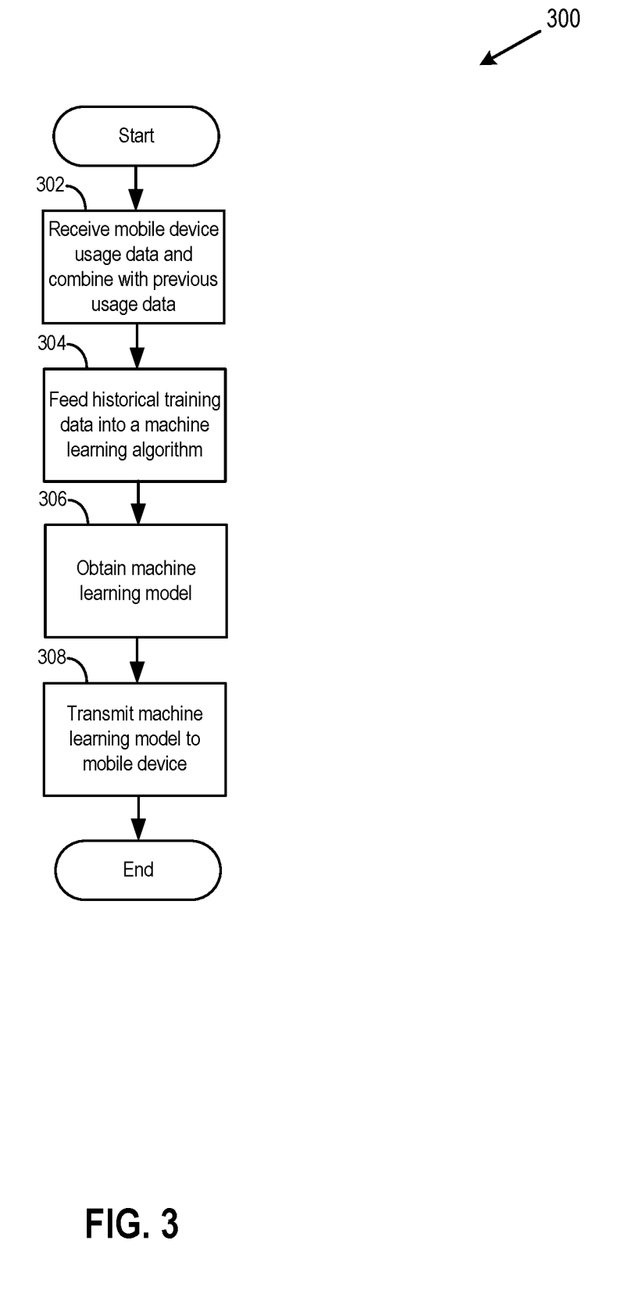
FIG. 3 depicts a flow diagram of a method of generating and training an ML model, according to an embodiment.

FIG. 3 depicts a flow diagram of a method 300 of generating and training the ML model 106, according to an embodiment. The method 300 is an expansion of block 202 of the method 200 of FIG. 2. The method 300 may be performed by the ML training module 128. The method 300 may be performed when enough of an amount of usage data 112 has been received to reliably train a neural net so as to generate a trained ML model 106. The method 300 may also be performed when an amount of new usage data 112 has been received to warrant re-generating and re-training a new ML model 106 in light of new data, after a previous ML model 106 had already been generated and provided to mobile device 102.

At block 302, ML training module 128 received usage data 112 from mobile device 102. The received usage data 112 may be usage data associated with one or more scheduled actions on the calendar 110, the actions having been scheduled prior to collecting data relating to each scheduled action. As part of block 302, if previous usage data exists, such as on server 124, then ML training module 128 combines the new usage data 112 with previous usage data to obtain a collection of data that is to be used to generate and train ML model 106. The collection of data that is to be used to generate and train ML model 106 may be referred to herein as the historical training data 132. As part of block 302, if previous usage data does not exist, then ML training module 128 does not combine the new usage data 112 with previous usage data. Optionally, as part of block 302, ML training module 128 may process some or all of the usage data and/or historical training data to obtain processed data that may be used to generate and train ML model 106. For example, ML training module 128 may use a voice-to-text engine to convert sound data from a microphone of mobile device 102 to natural speech, or may use the mood identifier 136 to obtain mood data. The natural speech and mood data may then be used as data that is fed into a neural network to generate and train the ML model 106.

At block 304, the ML training module 128 feeds the historical training data 132 into a neural net to generate and train ML model 106. ML training module feeds into a neural net data that includes (a) input training data of location data, time and/or a time range, data of some or all sensor(s) 120, and (b) output training data consisting of an associated action scheduled on the calendar 110, the scheduling having been for the time that is used as an input data into the neural net. In this manner, the ML model 106 can correlate data provided by the sensors in the mobile device (e.g., a microphone, a proximity sensor, ambient light sensor, camera, accelerometer, gyroscope, compass, barometer, and pressure sensitive display) to a scheduled task or action that is performed by the user (e.g., brushing teeth, going to bathroom, going to bus stop and waiting for school bus, doing homework, eating, calling a therapist or trusted person, meditating, taking medication, and the like). Put differently, block 304 can be used to associate different types of sensor data to a specific task that the user should perform. Optionally, input training data may also include data obtained by processing some or all usage data 112 and/or historical training data, and the processed data may include natural language data and/or mood data.

At block 306, the ML training module 128 completes training the neural net, and obtains a generated and trained ML model 106.

At block 308, server 124 transmits the generated and trained ML model 106 to mobile device 102. As part of block 308, mobile device 102 receives the ML model 106, stores the ML model 106 within memory 104 and/or storage 108, and executes the ML model 106 within memory 104 on mobile device 102. If a previously generated ML model 106 exists on mobile device 102, then mobile device 102 replaces the old ML model 106 with the new ML model 106. If a previously generated ML model 106 does not exist on mobile device 102, then mobile device 102 does not replace an old ML model 106 with the new ML model 106. After block 308, the method 300 ends.

Figure 4:
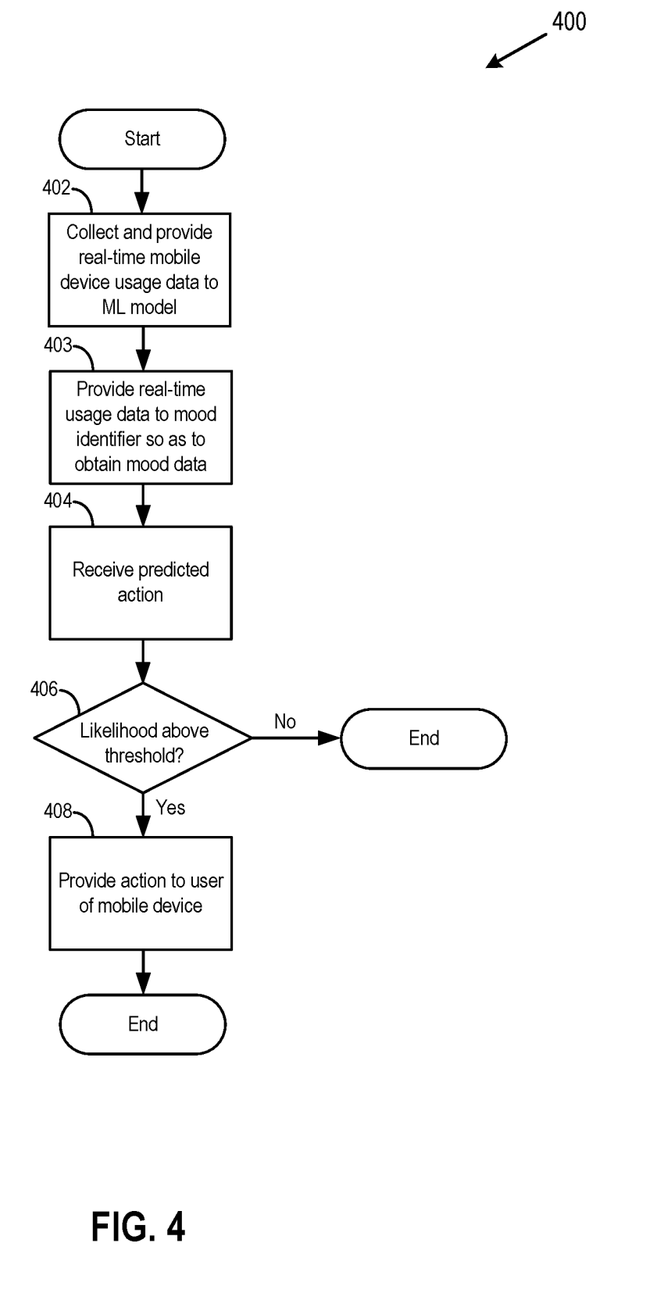
FIG. 4 depicts a flow diagram of a method of using the real-time data by a trained ML model to predict an action to be taken by a user of a mobile device, according to an embodiment.

FIG. 4 depicts a flow diagram of a method 400 of using the real-time data by the trained ML model 106 to predict an action to be taken by a user of the mobile device 102, according to an embodiment. The method 400 is an expansion of block 206 of the method 200 of FIG. 2, according to an embodiment. The method 400 may be performed by the mobile device 102.

At block 402, the mobile device 102 collects real-time environment usage data of the mobile device 102 by a user, the real-time usage data comprising real-time location, time, and sensor data for a predefined period of time. Mobile device 102 provides the real-time data to the ML model 106. In an embodiment, prior to providing real-time data to the ML model 106, mobile device 102 processes some or all of the real-time data to generate higher level characterizations of the real-time data, such as to obtain text from audio data generated by a microphone or classifying the users motions measured by the accelerometer as being "fidgety" or a spasm. The higher level characterizations are provided to the ML model 106, either together with the raw, real-time data used to obtain the higher level characterizations, or instead of the real-time data.

At block 403, the mobile device 102 provides real-time data collected at block 402 to a trained mood identifier 136. The mood identifier uses the real-time data to determine a mood of the user of the mobile device 102. For example, the mood identifier 136 may determine from images taken of the user than the user has an excited, sad, or upset facial expression, and can generate data that indicates such a mood or emotional state. As part of block 403, mobile device and/or mood identifier 136 provide the generated mood data to Ml model 106.

At block 404, the mobile device 102 receives a predicted or determined action that the user of mobile device 102 is expected to take at this time, based on the data provided to ML model 106 at block 402. The data used by ML model 106 to make the prediction may be environment data collected at block 402, mood data generated at block 403, or both. That is, the ML model 106 generates a suggested action, such as one that can mitigate a an emotional state or a symptom of autism the user is currently experiencing. For example, a parent might know that their autistic child (the user of the mobile device 102) gets into a negative emotional state whenever the autistic child rides a bus. The parent knows that the child rides the bus every day at 8 am. The parent might then schedule an action for every day on calendar 110 for the child to call a trusted person (e.g., friend, parent, etc.) at 8 am every day. ML model 106 may then associate the environmental and mood data of the child shortly before 8 am with a call to a trusted person. The environmental data may be associated with, for example, accelerometer and gyroscope data that indicates movement of the bus. Mood data (as generated by mood identifier 136), may also be based on movement, such as fidgetiness of the child, or may be based on other data of sensor(s) 120, such as camera and/or microphone data. After ML model 106 is trained, if a child gets on a bus, ML model may recognize that and recommend that the child call a trusted person. As such, emotional states associated with autism may be mitigated by actions that are suggested, determined, or predicted by a trained ML model 106.

For another example, the ML model 106 may correlate stuttering to a suggested action of taking medication earlier than she would otherwise, which may help the child to better express herself. One advantage of method 400 is that it can adapt to different situations and environments. Because the mobile device 102 can continually provide updated sensor data to the ML model 106, the model 106 can provide suggested actions that can mitigate the negative effects of autism and help the user to adapt to a new environment.

In an embodiment, mobile device 102 may receive an "inconclusive" message rather than a predicted action, if the data provided at block 402 is not associated with any action on which mobile device 102 had been trained. In another embodiment, mobile device 102 may receive an action along with a confidence score or likelihood score. The confidence or likelihood score may be expressed in the form of a percentage. As part of block 404, ML model 106 evaluates the data provided at block 402 to predict or determine an action to be taken by the user of the mobile device 102.

At block 406, mobile device 102 compares a likelihood score from block 404 to a threshold value. The threshold value may be predefined, and may be for example, 10%, 20%, 50%, 70%, 90%, 95%, or 99%. If the likelihood score is below the threshold, the method 400 ends. If the likelihood score is at or above the threshold, the method 400 continues to block 408. It should be noted that block 406 is optional, and method 400 may continue to block 408 directly from block 404, as long as a predicted action is received rather than an "inconclusive" message.

At block 408, the predicted action is provided to the user of the mobile device 102, such as by voicing the action or displaying the action on a screen. Optionally, as part of block 408, the user of the mobile device 102 performs the predicted action. After block 408, the method 400 ends.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., ML model 106, ML training module 128) or related data available in the cloud. For example, the ML model 106 and/or ML training module 128 could execute on a computing system in the cloud and train a neural net using historical training data 132 that is stored at a location in the cloud, so as to provide a predicted action to a user of the mobile device 102. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method for predicting an action to be taken by a user of a mobile device, comprising:
   receiving real-time usage data of the mobile device, the real-time usage data indicating at least (a) an emotional state of the user, wherein the emotional state is indicative of autism spectrum disorder and (b) indicators of the environment of the user; and
   evaluating data comprising the real-time usage data of the mobile device using a machine learning (ML) model to output a suggested action to be performed by the user, wherein the suggested action mitigates a negative impact on the user of a symptom of the autism spectrum disorder, and further wherein the ML model is trained using historical training data comprising (a) output training data that includes a scheduled action on a calendar and (b) input training data comprising historical usage data of the mobile device by the user, wherein training the ML model comprises:
   determining a first time of a first scheduled action on the calendar, wherein the calendar corresponds to a user having autism spectrum disorder;
   collecting first usage data, for the user having autism spectrum disorder, from a defined period of time prior to the first time; and
   training the ML model using the first usage data as input and the first scheduled action as output, wherein the ML model learns to correlate the first usage data to the first scheduled action.

2. The method of claim 1, wherein the historical usage data comprises time data, location data, and data from at least one sensor of sensors of the mobile device.

3. The method of claim 2, wherein the sensors of the mobile device comprise a proximity sensor, an ambient light sensor, a camera, an accelerometer, a gyroscope, a compass, a barometer, or a pressure sensitive display.

4. The method of claim 2, wherein the historical training data further comprises mood data obtained from a mood identifier, wherein mood data indicates an emotional state of the user, and further wherein the mood identifier is a second machine learning model that is generated by training a neural net using data that includes the historical usage data, wherein the historical usage data is used to generate the ML model, and the ML model performs the outputting of the suggested action.

5. The method of claim 1, wherein the data comprising the real-time usage data further comprises a higher level characterization, wherein the higher level characterization is obtained by processing some or all of the real-time usage data.

6. The method of claim 5, wherein the higher level characterization comprises at least one of (a) text obtained from audio generated by a microphone of the mobile device, (b) classifying motion data measured by an accelerometer of the mobile device as being fidgety or a spasm.

7. The method of claim 6, the method further comprising, comparing a confidence score to a predefined threshold, and based on the comparison, providing the suggested action to be performed to the user.

8. The method of claim 1, wherein the ML model comprises at least one of a feedforward neural network, a regulatory feedback neural network, a radial basis function neural network, a recurrent neural network, or a modular neural network.

9. A system, comprising:
   a mobile device;
   a machine learning (ML) model;
   historical training data;
   a calendar;
   a processor, wherein the processor is programmed to carry out a method of predicting an action to be taken by a user of the mobile device, the method comprising:
   receiving real-time usage data of the mobile device, the real-time usage data indicating at least (a) an emotional state of the user, wherein the emotional state is indicative of autism spectrum disorder and (b) indicators of the environment of the user; and
   evaluating data comprising the real-time usage data of the mobile device using a machine learning (ML) model to output a suggested action to be performed by the user, wherein the suggested action mitigates a negative impact on the user of a symptom of the autism spectrum disorder, and further wherein the ML model is trained using the historical training data comprising (a) output training data that includes a scheduled action on the calendar and (b) input training data comprising historical usage data of the mobile device by the user, wherein training the ML model comprises:
   determining a first time of a first scheduled action on the calendar, wherein the calendar corresponds to a user having autism spectrum disorder;
   collecting first usage data, for the user having autism spectrum disorder, from a defined period of time prior to the first time; and
   training the ML model using the first usage data as input and the first scheduled action as output, wherein the ML model learns to correlate the first usage data to the first scheduled action.

10. The system of claim 9, wherein the historical usage data comprises time data, location data, and data from at least one sensor of sensors of the mobile device.

11. The system of claim 10, wherein the sensors of the mobile device comprise a proximity sensor, an ambient light sensor, a camera, an accelerometer, a gyroscope, a compass, a barometer, or a pressure sensitive display.

12. The system of claim 10, wherein the historical training data further comprises mood data obtained from a mood identifier, wherein mood data indicates an emotional state of the user, and further wherein the mood identifier is a second machine learning model that is generated by training a neural net using data that includes the historical usage data, wherein the historical usage data is used to generate the ML model, and the ML model performs the outputting of the suggested action.

13. The system of claim 9, wherein the data comprising the real-time usage data further comprises a higher level characterization, wherein the higher level characterization is obtained by processing some or all of the real-time usage data.

14. The system of claim 13, wherein the higher level characterization comprises at least one of (a) text obtained from audio generated by a microphone of the mobile device, (b) classifying motion data measured by an accelerometer of the mobile device as being fidgety or a spasm.

15. The system of claim 14, the method further comprising, comparing a confidence score to a predefined threshold, and based on the comparison, providing the suggested action to be performed to the user.

16. The system of claim 9, wherein the ML model comprises at least one of a feedforward neural network, a regulatory feedback neural network, a radial basis function neural network, a recurrent neural network, or a modular neural network.

17. A computer program product for a method of predicting an action to be taken by a user of the mobile device, the computer program product comprising:
  a computer-readable storage medium having computer-readable program code embodied therewith, the computer-readable program code executable by one or more computer processors to:
  receive real-time usage data of the mobile device, the real-time usage data indicating at least (a) an emotional state of the user, wherein the emotional state is indicative of autism spectrum disorder and (b) indicators of the environment of the user; and
  evaluate data comprising the real-time usage data of the mobile device using a machine learning (ML) model to output a suggested action to be performed by the user, wherein the suggested action mitigates a negative impact on the user of a symptom of the autism spectrum disorder, and further wherein the ML model is trained using historical training data comprising (a) output training data that includes a scheduled action on a calendar and (b) input training data comprising historical usage data of the mobile device by the user, wherein training the ML model comprises:
  determining a first time of a first scheduled action on the calendar, wherein the calendar corresponds to a user having autism spectrum disorder;
  collecting first usage data, for the user having autism spectrum disorder, from a defined period of time prior to the first time; and
  training the ML model using the first usage data as input and the first scheduled action as output, wherein the ML model learns to correlate the first usage data to the first scheduled action.

18. The computer program product of claim 17, wherein the historical usage data comprises time data, location data, and data from at least one sensor of sensors of the mobile device.

19. The computer program product of claim 18, wherein the sensors of the mobile device comprise a proximity sensor, an ambient light sensor, a camera, an accelerometer, a gyroscope, a compass, a barometer, or a pressure sensitive display.

20. The computer program product of claim 18, wherein the historical training data further comprises mood data obtained from a mood identifier, wherein mood data indicates an emotional state of the user, and further wherein the mood identifier is a second machine learning model that is generated by training a neural net using data that includes the historical usage data, wherein the historical usage data is used to generate the ML model, and the ML model performs the outputting of the suggested action.

\* \* \* \* \*